United States Patent
Bernardin et al.

(10) Patent No.: US 12,092,903 B2
(45) Date of Patent: Sep. 17, 2024

(54) METHOD FOR ADAPTING OPHTHALMIC EQUIPMENT ACCORDING TO A WEARERS VISUAL EXPLORATION STRATEGY

(71) Applicants: Essilor International, Charenton-le-Pont (FR); UNIVERSITE DE MONTREAL, Montreal (CA)

(72) Inventors: Delphine Bernardin, Montreal (CA); Jocelyn Faubert, Montreal (CA); Romain Chaumillon, Montreal (CA); Eduardo Lugo, Montreal (CA); Sergio Mejia Romero, Montreal (CA)

(73) Assignees: Essilor International, Charenton-le-Pont (FR); UNIVERSITE DE MONTREAL, Montreal (CA)

( * ) Notice: Subject to any disclaimer, the term of this patent is extended or adjusted under 35 U.S.C. 154(b) by 761 days.

(21) Appl. No.: 17/283,458

(22) PCT Filed: Oct. 9, 2019

(86) PCT No.: PCT/EP2019/077317
§ 371 (c)(1),
(2) Date: Apr. 7, 2021

(87) PCT Pub. No.: WO2020/074566
PCT Pub. Date: Apr. 16, 2020

(65) Prior Publication Data
US 2022/0011596 A1 Jan. 13, 2022

(30) Foreign Application Priority Data
Oct. 9, 2018 (EP) .................................... 18306332

(51) Int. Cl.
*G02C 7/02* (2006.01)

(52) U.S. Cl.
CPC ............. *G02C 7/027* (2013.01); *G02C 7/025* (2013.01)

(58) Field of Classification Search
None
See application file for complete search history.

(56) References Cited

U.S. PATENT DOCUMENTS 6,827,443 B2 * 12/2004 Fisher .................... G02C 7/061
351/209
6,974,414 B2 12/2005 Victor
(Continued)

FOREIGN PATENT DOCUMENTS

EP         1 747 750 A1    1/2007
JP       2003-523244 A     8/2003
(Continued)

OTHER PUBLICATIONS

International Search Report and Written Opinion issued on Nov. 11, 2019 in PCT/EP2019/077317 filed on Oct. 9, 2019.
(Continued)

*Primary Examiner* — Robert E. Tallman
(74) *Attorney, Agent, or Firm* — Oblon, McClelland, Maier & Neustadt, L.L.P.

(57) ABSTRACT

A system and method for determining an adapted ophthalmic device for a wearer, the method including acquiring a set of parameters values relating to the wearer, determining at least a task to be performed by the wearer involving visual exploration, using a computing system, determining a value of a criterion assessing an efficiency of the wearer's visual exploration strategy for the task, and determining an optical design of an ophthalmic device to be worn by a wearer according to the determined value of the criterion.

20 Claims, 10 Drawing Sheets

(56) References Cited

U.S. PATENT DOCUMENTS

| | | | |
|---|---|---|---|
| 7,828,433 | B2 | 11/2010 | Katzman et al. |
| 8,303,113 | B2 | 11/2012 | Esser et al. |
| 9,395,543 | B2 | 7/2016 | Lamb et al. |
| 2003/0107707 | A1 | 6/2003 | Fisher et al. |
| 2010/0097570 | A1 | 4/2010 | Katzman et al. |
| 2010/0157242 | A1 | 6/2010 | Esser et al. |
| 2011/0001925 | A1 | 1/2011 | Drobe et al. |
| 2014/0148707 | A1 | 5/2014 | Encaoua et al. |
| 2017/0059886 | A1 | 3/2017 | Fayolle et al. |
| 2017/0115513 | A1 | 4/2017 | Baranton et al. |

FOREIGN PATENT DOCUMENTS

| | | |
|---|---|---|
| JP | 2011-513798 A | 4/2011 |
| JP | 2011-125692 A | 6/2011 |
| JP | 2013-529792 A | 7/2013 |
| JP | 2017-507370 A | 3/2017 |
| WO | WO 01/62139 A1 | 8/2001 |
| WO | WO 2011/001925 A1 | 1/2011 |
| WO | WO 2015/124574 A1 | 8/2015 |

OTHER PUBLICATIONS

Pincus, "Approximate entropy as a measure of system complexity", Proc. Natl. Acad. Sci., 1991, vol. 88, pp. 2297-2301.

Abasolo et al., "Approximate Entropy of EEG Background Activity in Alzheimer's Disease Patients", Intelligent Automation and Soft Computing, 2003, vol. 9, No. X, pp. 1-11 (with cover sheet).

Pincus et al., "Physiological time-series analysis: what does regularity quantify?", Modeling in Physiology, 1994, pp. H1643-H1656.

\* cited by examiner

METHOD FOR ADAPTING OPHTHALMIC EQUIPMENT ACCORDING TO A WEARERS VISUAL EXPLORATION STRATEGY

FIELD OF THE INVENTION

The relates to a method for determining adapted ophthalmic equipment for a wearer, according to at least a visual exploration strategy used by the wearer in a situation, and to a system for determining such an adapted ophthalmic equipment.

BACKGROUND OF THE INVENTION

During everyday life, a person constantly explores its visual environment in order to detect, anticipate, observe, read and follow any relevant information for making a decision and acting. In order to explore the visual environment, the eyes of the person are prone to make a number of elementary motions being:
  A fixation, which is the set of coordinated motions of the eyes and the head to maintain the visual gaze direction towards a single location,
  A saccade, which is a very quick movement of the eyes to change the visual gaze direction from one location to another, and
  A smooth pursuit, which is the movement of following an object moving in the visual field.

During a visual exploration of the environment, the eyes perform a series of saccades and fixations, wherein the fixations step can for example be longer or shorter depending on the information that has to be processed from a zone of interest. The visual exploration thus involves a great number of transitions between different eyes eccentricities, vision distances and planes of accommodation in coordination with the head.

The visual exploration strategy also depends on the purpose of the exploration, on the environment, on the type of task to perform, etc. According to an example, the visual exploration strategy of a person can vary whether the person has to look at a person or written information, or if the person has to perform an activity if the person is driving, or walking, or texting while walking, etc.

According to another example, the visual exploration strategy is different according to the context, i.e. the workload of the task, the daytime, or the weather, etc.

Additionally, the visual exploration strategy is different from a person to another, and can vary according to multiple factors such as age, motor, sensorial or cognitive capacities and according to an ophthalmic device worn by the person.

For instance, progressive addition lenses designed for prebyopic wearers include a far-vision zone, a near-vision zone and an intermediate-vision zone, and the transitions between those zones generate aberrations, notably leading to blur and distortion.

Known solutions already exist to personalize the design of progressive addition lenses, according to the prescription of the wearer and more generally, according to the visual needs of the wearer.

For instance, methods are known from documents U.S. Pat. Nos. 8,303,113 and 7,828,433 according to which the visual need of a user is assessed in a mobility activity such as driving, by identifying the main zones of the environment that are watched by the user during the activity. An ophthalmic device is then designed, including specific zones configured according to the identified main zones of the environment.

These solutions only take into account the zones of the environment that are watched by the user in a static manner, and do not take into account the full visual exploration strategy, which also includes dynamic aspects such as:
  The repeatability and stability in the pattern of the eye, head, gaze motions in time,
  The succession of moves that are performed to check all the environment for detection of an event,
  The path followed by the visual gaze direction for switching from a zone of interest to another, including the number of saccades, their distribution and the intermediate spots which are looked at by the user between two main zones of interest, and its repeatability,
  The most important frequency in the gaze pattern and its organization,
  The motion of the eyes and the head while gazing at a constant main zone of interest, etc.

Accordingly, if a wearer's visual exploration strategy comprises a lot of moves within a given zone of interest or for switching between two zones of interest, an ophthalmic device designed according to the methods disclosed in these documents may not be adapted to the wearer and cause a fatigue or discomfort.

There is therefore a need for a solution to design personalized ophthalmic equipment which better take into account a wearer's personal visual exploration strategy.

SUMMARY OF THE INVENTION

The purpose of the invention is to provide a solution to the defects in the prior art.

In particular, one aim of the invention is to provide a method for optimizing the design of an ophthalmic equipment for a given wearer, taking into account the visual exploration strategy of the wearer.

The above-mentioned purpose is achieved by a combination of the characteristics described in the independent claims, and subordinate claims provide for specific advantageous examples of the invention.

A method for determining an adapted ophthalmic device for a wearer, is disclosed, comprising:
  acquiring a set of parameters values relating to the wearer,
  determining at least a task to be performed by the wearer involving visual exploration,
  using a computing system, determining a value of a criterion assessing an efficiency of the wearer's visual exploration strategy for said task, and
  determining an optical design of an ophthalmic device to be worn by a wearer according to the determined value of the criterion.

In an embodiment, the step of determining the value of the criterion assessing the efficiency of the wearer's visual exploration strategy for said task comprises:
  submitting the wearer to a test scenario involving the performance of said task in a determined environment, and
  recording, with at least one sensor, the wearer's visual exploration strategy during the test scenario, and
  evaluating the criterion assessing the efficiency of the wearer's visual exploration strategy from the recorded visual exploration strategy.

In an embodiment, the step of determining a value of a criterion assessing an efficiency of the wearer's visual exploration strategy further comprises comparing the evaluated criterion to a reference value, and the step of determining an optical design is performed according to the outcome of the comparison of the evaluated criterion and the reference value. The reference value may be calculated over a reference population, or may be a reference value for the wearer. In some embodiments, the reference value may assessed from the wearer's visual exploration strategy during a previous submission of the wearer to a test scenario involving the performance of the same task in the same determined environment, the wearer being equipped with a previous ophthalmic device or being devoid of any ophthalmic device.

In embodiments, the step of recording the wearer's visual exploration strategy comprises recording, at a determined frequency, the gaze direction or spot observed by the wearer. The step of recording the wearer's visual exploration strategy may further comprise recording, at a determined frequency, the motion of the eyes and of the head of the wearer.

In embodiments, the step of submitting the wearer to a test scenario involving the performance of said task in a determined environment is performed by submitting the wearer to a virtual situation simulated using a virtual reality equipment. The test scenario may be configured based on:
 the selection of the task to be performed while the visual exploration strategy is recorded,
 the selection of the environment, in which the task is performed, and
 the selection of at least one additional parameter affecting the visual exploration involved during the test situation, among a group of parameters comprising:
 duration of the test scenario,
 visual scene complexity of the test scenario,
 number and disposition of zones of interest to be explored in the environment while performing the selected task,
 mental work load,
 type and number of decisions to be performed by the wearer during the test scenario.

The task to be performed during the test scenario may be selected among the group consisting of:
 Driving,
 Walking,
 Cycling,
 Walking up or down stairs,
 Climbing on or off a ladder,
 Practicing a sport.

In an embodiment, the step of determining the value of the criterion assessing the efficiency of the wearer's visual exploration strategy for said task, may be performed using a system comprising a computer and a database storing reference values of the criterion assessing the visual exploration strategy efficiency for each of a plurality of populations of wearers and each of a plurality of tasks, and the step of determining the value of the criterion assessing the efficiency of the visual exploration strategy of the wearer comprises interrogating, with the computer, the database with input data comprising the set of parameter values relating to the wearer and the task, to retrieve a reference value of the criterion for a population corresponding to the wearer.

In embodiments, the step of determining an optical design comprises choosing, among a plurality of designs of an ophthalmic device, a design maximizing the efficiency of the wearer's visual exploration strategy for the task.

In embodiments, wherein the criterion assessing the efficiency of the wearer's visual exploration strategy is chosen among the group consisting in:
 an approximate entropy of the visual exploration,
 Power based index of the visual exploration or of the approximate entropy of the visual exploration,
 a number, weight and redundancy of frequencies involved in the visual exploration pattern, determined from a spectral analysis of the recorded visual exploration or on the approximate entropy of the visual exploration,
 an evolution on time of the approximate entropy of the visual exploration, or
 an efficiency in transiting from one observed zone of interest to another.

In an embodiment, the method comprises the determination of the value of at least two different criteria assessing an efficiency of the wearer's visual exploration strategy for said task, and determining an optical design of an ophthalmic device to be worn by a wearer according to the determined values of the criteria.

In an embodiment, the criterion assessing the efficiency of the wearer's visual exploration strategy is the efficiency in transiting from one observed zone of interest to another, and the evaluation of the criterion can comprise:
 determining a plurality of areas of interest of the wearer's field of view,
 recording, with at least one sensor, the wearer's visual exploration strategy during the test, and computing the proportion of the occurrences within the areas of interest.
 forming a Markov Chain of the areas of interest, wherein each area of interest is associated to a set probabilities to transit to other zones at a next time, and
 evaluating the efficiency in transiting from one area of interest to another from a processing of the Markov Chain of the areas of interest.

In an embodiment, the processing of the Markov Chain comprises computing an entropy of the stationary distribution of the areas of interest.

In an embodiment, the method comprises:
 evaluating approximate entropy of gaze direction or spot observed by the wearer,
 evaluating approximate entropy of the motion of the eyes of the wearer,
 evaluating approximate entropy of the motion of the head of the wearer,
and wherein the step of determining an optical design of an ophthalmic device to be worn by a wearer is performed based on the approximate entropy of gaze direction or spot observed by the wearer, and based on the relative values of the approximate entropy of the motion of the eyes and the approximate entropy of the motion of the head.

According to another embodiment of the invention, a system for determining an optimized ophthalmic device for a wearer is disclosed, the system comprising a computing device configured to:
 receive a set of parameter values relating to the wearer,
 receive additional input data comprising at least identification of a task to be performed by the wearer and involving visual exploration, and
 determine a value of a criterion assessing an efficiency of the wearer's visual exploration strategy for said task from the set of parameter values and the additional input data.

In an embodiment, the system may further comprise:
 a virtual reality device configured to run a test scenario selectable among a plurality of test scenarios,
 at least one sensor configured to record the visual exploration strategy involved by the wearer while using the virtual reality device running the test scenario, and
the computing device is configured to compute a value of a criterion assessing the efficiency of the visual exploration strategy involved by the wearer during the test scenario.

For instance, the virtual reality device may be a head-mounted virtual reality helmet, and the sensor may comprise at least one of the following:
- at least one sensor configured to record the gaze direction or the eyes motions of the wearer,
- at least one sensor configured to record the motion of the virtual reality helmet, and
- a camera having a fixed direction, being affixed to the virtual reality helmet.

The method according to the invention comprises the assessment of the efficiency of a wearer's visual exploration strategy involved by the performance of a task, in order to adapt the ophthalmic equipment.

The assessment of the efficiency of the strategy takes into account the dynamics of the visual exploration. More specifically, the efficiency of the visual exploration strategy takes into account not only the main zones of interest of a person, but also the paths of the gaze direction within or between said zones, including "parasitic" movements of the eyes.

Assessing the efficiency of the visual exploration strategy thus allows personalizing or selecting ophthalmic equipment which preserves or enhances this efficiency, for a reduced fatigue and improved comfort.

In embodiments, the efficiency may be assessed by exposing the wearer to a test situation, which can for example be simulated by a virtual reality device, in which numerous parameters may be controlled such as, the task to be performed by the wearer and the environment in which it has to be performed. The assessed efficiency may then be compared to a reference and the determination of the design of an ophthalmic equipment can be performed according to the assessed efficiency and to a reference efficiency.

The proposed method allows taking into account wearer personal parameters such as visual, cognitive or motor capacities, as well as the wearer's needs for a particular task, in order to adapt an ophthalmic equipment.

DESCRIPTION OF THE DRAWINGS

For a more complete understanding of the description provided herein and the advantages thereof, reference is now made to the brief descriptions below, taken in connection with the accompanying drawings and detailed description, wherein like reference represent like parts.

FIG. 5b represents a frequency decomposition of the signal of FIG. 5a.

FIG. 6b represents an example of visual exploration recorded using the test situation of FIG. 6a.

DETAILED DESCRIPTION OF AT LEAST ONE EMBODIMENT OF THE INVENTION

As will be described in greater details below, the invention proposes assessing the efficiency of the visual exploration strategy of a wearer in order to adapt an ophthalmic equipment, i.e. either in selecting a personalized design or personalizing an ophthalmic equipment to the needs of a wearer.

The diversity of visual exploration mechanisms and the standard parameters of measurement of the latter make it difficult to evaluate the needs, or performance of users.

The assessment of efficiency of visual exploration strategy allows evaluating the dynamic organization of the visual exploration, i.e. not only considering isolated movements to look at a target, but the general strategy that is involved by a user to interact with its visual environment, understand the latter and make decision. It can then be used to personalize an ophthalmic device for a wearer, in order either to improve the strategy or to take into account the strategy to make a specific task easier or more comfortable to perform.

Figure 1:
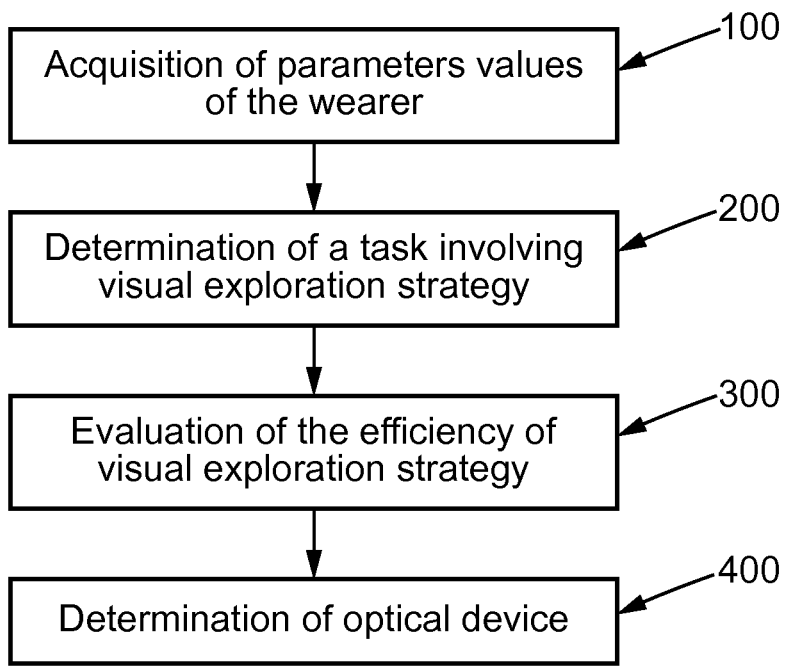
FIG. 1 schematically represents the main steps of a method for determining an adapted ophthalmic device for a wearer according to an embodiment of the invention, FIG. 2 schematically represent an embodiment of a step of evaluating a criterion assessing the efficiency of a visual exploration strategy.

With reference to FIG. 1, the main steps of a method for determining an adapted ophthalmic equipment according to an embodiment of the invention will now be described.

Figure 7:
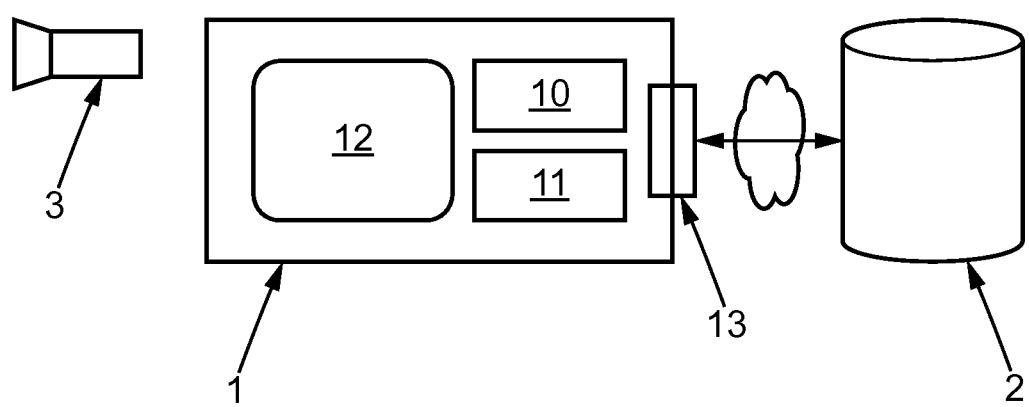
FIG. 7 schematically represents an example of system for implementing the method according to an embodiment of the invention.

A first step 100 comprises acquiring a set of parameters values relating to the wearer. At least part of the parameter values may be measured, or obtained from a questionnaire or from a database, or extracted from online data of the wearer. Preferably, this step is performed by a computing device 1 schematically shown on FIG. 7, and comprising:
- A calculator 10 comprising at least one processor or microprocessor, microcontroller, etc.
- a memory 11,
- a human-machine interface 12, such as a display screen, tactile or not, and/or a keyboard, and
- an interface 13 for connection with a telecommunication network such as internet.

The collecting unit may be a software module stored on the memory and run by the calculator, for instance an application software configure to display a questionnaire for inputting the parameter values of the wearer, or configure to retrieve the data from a database based on, for instance, an identifier of the wearer.

The parameters which values are acquired may comprise one or several of the following:
- age,
- gender,
- biometric parameter (for instance interpupillary distance)
- activities performed by the wearer,
- type environment in which the activities are performed, The parameters may also comprise additional parameters regarding the visual or motor or cognitive abilities or needs of the wearer such as:
- visual prescription,
- current ophthalmic device,
- perceptual and cognitive skills,
- motor or of mobility performances.

A second step 200 comprises the determination of at least one task to be performed by the wearer, involving visual exploration. Typically, said task is a task that is repeatedly performed by the wearer in its daily life. In an embodiment, this task is a task that is visually demanding for a wearer, and according to which an ophthalmic device of the wearer has to be adapted. Moreover, it may be a continuous task involving an interaction between the wearer and its environment, and involving a number of secondary tasks such as detecting obstacles, reading, eating or drinking, texting, etc.

According to non-limiting examples, said task may be any of the following:
Driving,
Walking,
Cycling,
Walking up or down stairs,
Climbing on or off a ladder,
Practicing a sport,
Mobility in virtual environment such as gaming.

Step 200 may also be performed using the collecting unit described above.

A third step 300 comprises the determination of a value of a criterion assessing an efficiency of the wearer's visual exploration strategy for the task identified at step 200.

With reference to FIGS. 2a and 2b, this step may be performed according to various embodiments.

According to a first embodiment, schematically represented in FIG. 2a, this step is performed by submitting 310 the wearer to a test scenario involving the performance, by the wearer, of the task determined at step 200, in a determined environment, and recording 320 the visual exploration performed by the wearer while submitted to this test scenario.

The test scenario is the exploration, by the wearer, of the determined environment while accomplishing the task.

Thus, each test scenario is preferably parameterized with:
A main task to be performed, which corresponds to the task determined at step 200 but does exclude secondary tasks to be performed during the test scenario, and
An environment in which the main task is performed.

One or more additional parameters may be used to configure the test scenario, such as:
duration of the test scenario,
visual scene complexity of the test scenario,
number and disposition of zones of interest to be explored in the environment while performing the selected task,
mental work load,
type and number of decisions to be performed by the wearer during the test scenario.

According to a first example, the test scenario may be a sequence during which the wearer drives a car. The environment may be selected according to several types of environment such as: rural, urban, highway.

The test scenario may further be parameterized by adding secondary tasks such as:
looking at a GPS device to follow a path,
reading a message on the car's dashboard,
avoiding an obstacle,
reading signpost on the street, etc.

According to a second example, the test scenario may be a sequence during which the wearer walks. The environment may be selected according to several types of environment such as: rural, urban, nature (for instance mountain hiking).

The test scenario may further be parameterized by adding secondary tasks such as:
reading a sign,
avoiding an obstacle,
texting while walking, or crossing a street, etc.

According to an embodiment, the environment in which the test scenario is implemented is a real environment, i.e. the wearer is actually driving or walking or performing the task.

Figure 6A:
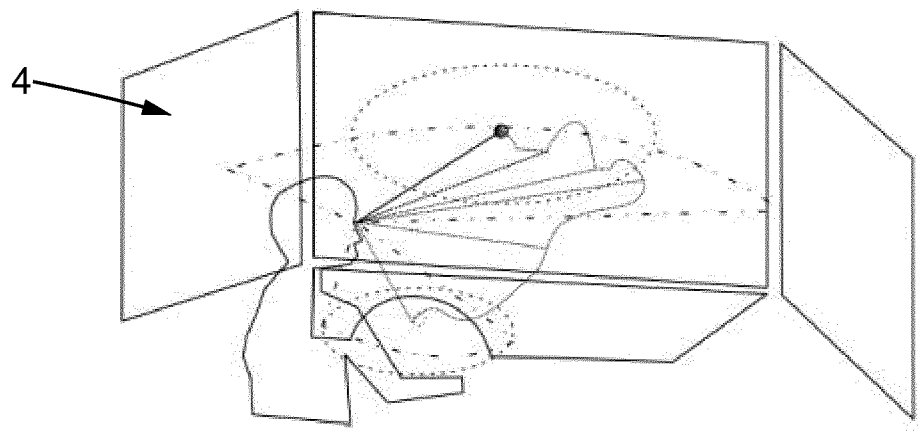

According to another embodiment, as shown schematically in FIG. 6a, the environment in which the test scenario is implemented is a virtual environment, which is simulated by a virtual reality equipment 4. In that case, the task to be performed can also be performed in the virtual environment. For instance, in the case of driving, the interior of the car is also simulated by the virtual reality equipment and the wearer is given controlling devices enabling to virtually drive the car.

The recording 320 of the visual exploration is preferably performed by recording the gaze direction of the wearer, or the spot gazed at by the wearer, during the test scenario, using a recording device 3. More specifically, the gaze direction is recorded at a fixed, determined frequency during the test scenario to enable analysis of the dynamics of the visual exploration. For instance, the frequency at which the gaze direction is recorded is at least 25 Hz, preferably at least 120 Hz, for example 1 kHz.

The recording device 3 may be worn by the wearer or located at a distance from the latter, for instance mounted on a screen on which is displayed a virtual environment, mounted on a dashboard of a car driven by the wearer, etc. The recording device 3 may also be equipped with a system for recording the visual scene of the test scenario, and/or a system for recording the motion of the head or the behavior of the wearer.

According to an exemplary embodiment, the recording device 3 may comprise at least one sensor or camera adapted to record the motion of the eyes, and optionally at least one sensor adapted to also record the motion of the head.

For instance, the recording device 3 may be an eye-tracker integrated into a virtual reality helmet. According to another example, the recording device may be a pair of glasses comprising an eye-tracker and optionally a gyroscope and/or accelerometer. The recording device may also be an eye-tracker mounted on a support which is not worn by the wearer but located at a fixed position relative to the wearer, such as on a screen or dashboard.

Solutions comprising hardware and software components and marketed by the company SensoMotoric Instruments (SMI) may be used as eye-tracking recording devices.

In an embodiment in which an eye tracker and a system for recording head position are used, the gaze direction is inferred as follows. A model-based approach is adopted, comprising the following assumptions:
the eyeball is spherical and the eye center is at a fixed point relative to the head model,
all the eye points, including the pupil, are detected using the eye-tracker, and
the eye is open and therefore all the eye contour points can be considered.

The determination of gaze direction is performed by estimating the 3D position of the pupil from the eye contour points, and then estimating the 3D gaze direction from the pupil position and the head center. A calibration is performed preliminary in order to establish a correspondence between the orientation of the pupil and the corresponding point in space which is looked at.

Finally, the gaze angles with respect to the camera coordinate system are computed.

Figure 3A:
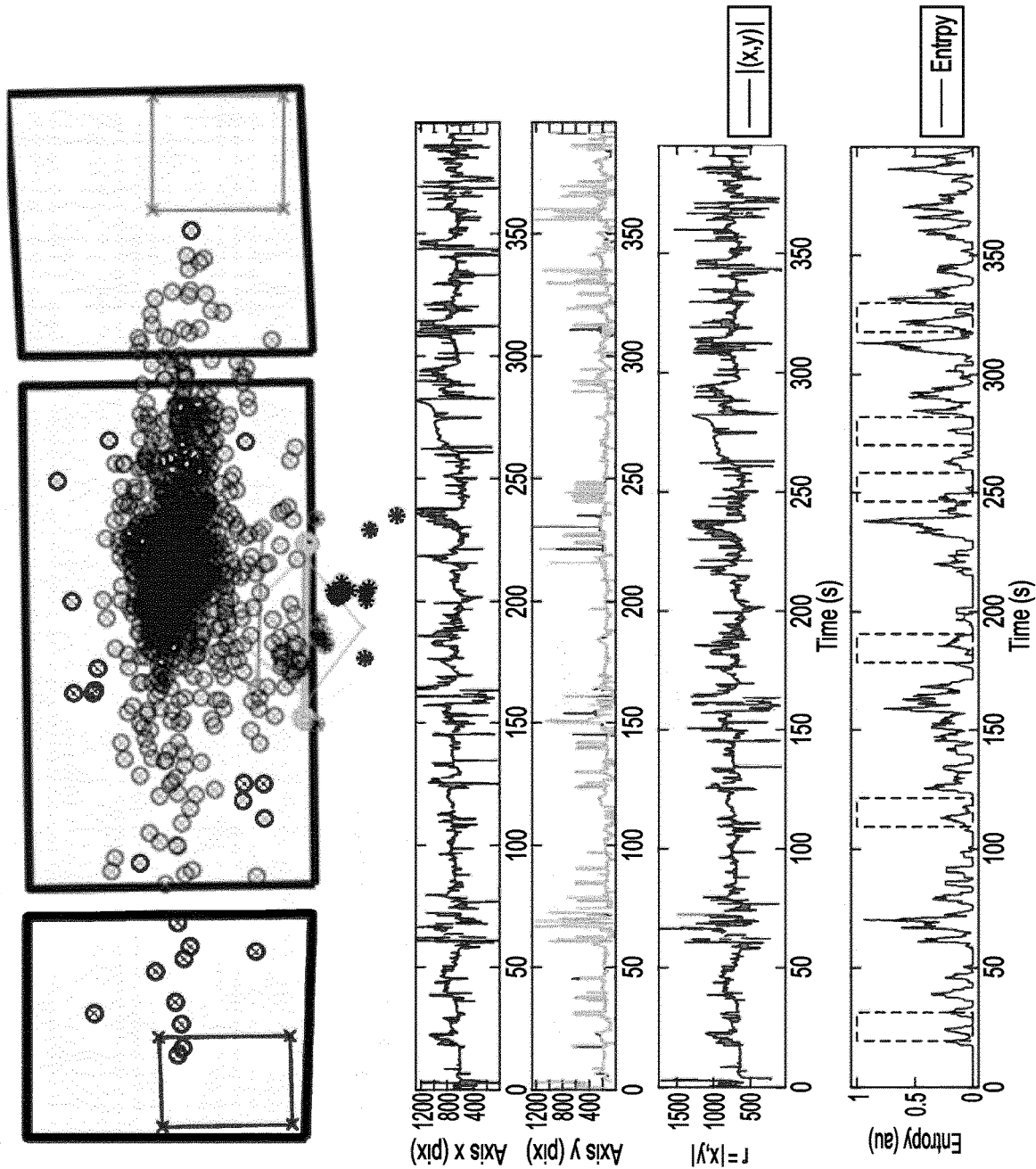
FIGS. 3a and 3b are representations of the visual exploration strategy of two different persons for a common task, and corresponding processing to infer the value of a criterion assessing the efficiency of the visual exploration strategy.
Figure 3B:
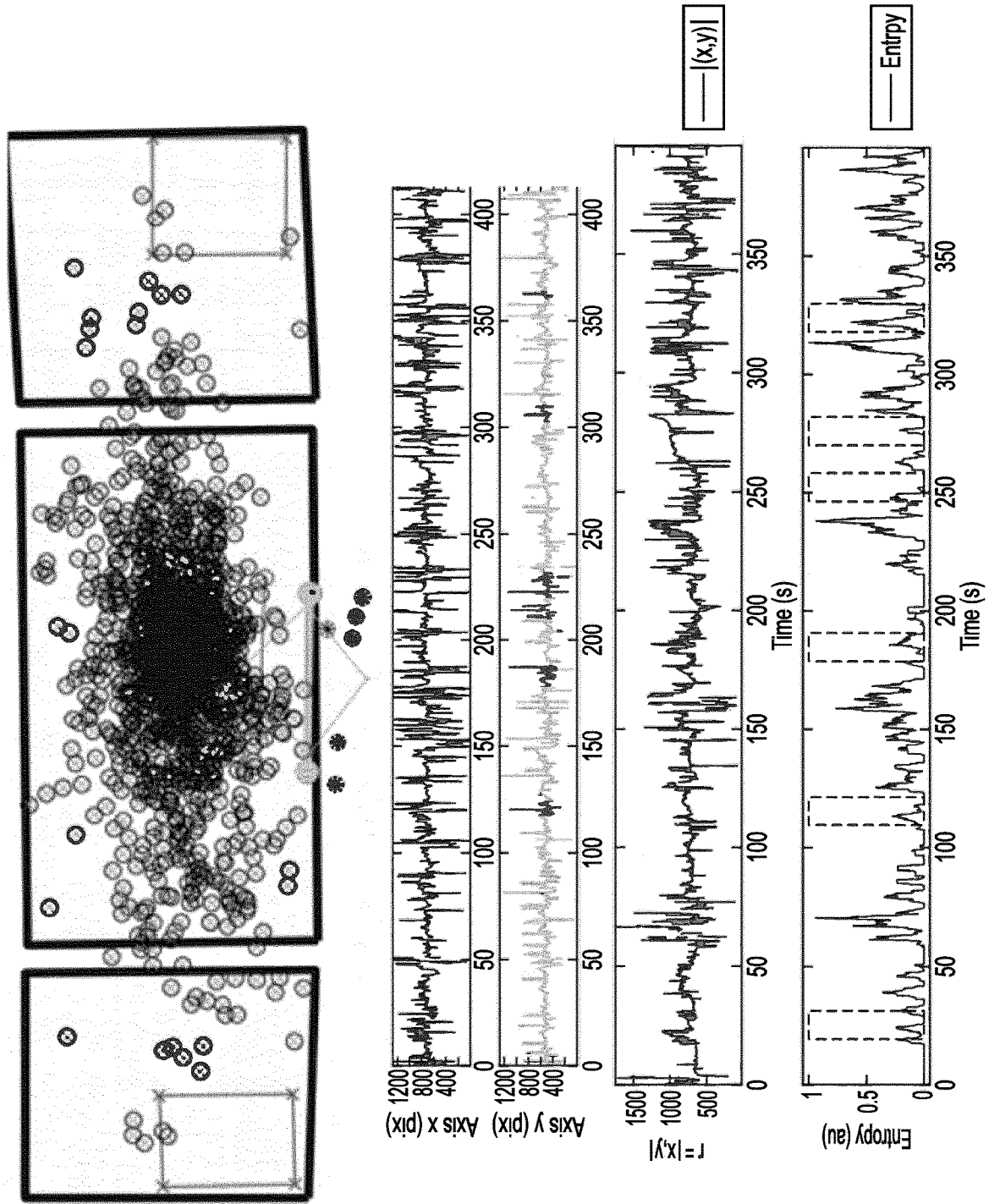

With reference to FIGS. 3a and 3b, the visual exploration of two different persons has been recorded in an identical test scenario involving a simulated environment displayed on several screens arranged around the person. The first part of each figure is a representation of the spots of the virtual environment that were gazed at during each test scenario.

Regarding the graphs shown on the figures, the first one represents the evolution with time of the x axis coordinate of the spot gazed at by the person, and the second line represents the evolution with time of the y axis.

The third graph represents r=|x,y|, which is the amplitude of the vector of the gaze direction projected on a plane which corresponds for instance to a screen or to the visualized scene.

Optionally, before further processing, a filtering of the raw data of gaze direction may be performed in order to remove noise. The filtering may comprise the use of a median filter and/or a passband filter. As a non-limiting example a passband filter of between 1 Hz to 10 Hz may be used.

During a subsequent step 330, at least one criterion assessing the efficiency of the visual exploration strategy is evaluated based on the recorded visual exploration strategy involved by the wearer during the test scenario.

In this embodiment, the evaluation of the criterion is performed by the computing device since it implies processing series of data.

The criterion is preferably chosen among the following list:
- an approximate entropy of the gaze direction or location of the spot observed by the wearer,
- a number of frequencies involved in the visual exploration pattern, determined from a spectral analysis of the recorded visual exploration strategy,
- a fatigue evaluated from an evolution on time of an approximate entropy of the visual exploration, or
- an efficiency in transiting from one observed zone of interest to another.

The various criteria will be commented in more details below.

Approximate entropy was introduced in the following published articles:
- S. M. Pincus, "Approximate entropy as a measure of system complexity", Proceedings of the National Academy of Sciences of the USA, vol. 88, pp. 2297-2301, 1991,
- S. M. Pincus and A. L. Goldberger, "Physiological time series analysis: what does regularity quantify?", American Journal of Physiology (Heart and Circulatory Physiology), vol. 266, pp. H1643-H1656, 1994,
- D. Abasolo, R. Hornero, and P. Espino, "Approximate entropy of EEG Background Activity in Alzheimer's disease patients", Intelligent Automation and Soft Computing, 15(4), pp. 591-603, 2009.

The approximate entropy is a function that measures the regularity of the values in a signal or a system, that is, quantifies the repeatability of the values belonging to a signal. For instance, if a signal provides repetitive patterns, then the signal is stable and the approximate entropy is low.

Approximate entropy can be used as a criterion for evaluating the efficiency of the visual exploration if calculated based on the distribution of the movement in the gaze direction.

The computation of the approximate entropy can be done as follows.

First, the input data for computing approximate entropy comprises a time series of N data points $\{x(n)\}=x(1), x(2), x(3), \ldots, x(N)$ where $n=1, 2, 3 \ldots, N$, where each data point typically comprises the gaze direction in polar coordinates or along x and y orthogonal axes (representing the spot which is gazed at).

A window of length 'm', m representing the length of compared runs of data, and a positive real number r, specifying a filtering level or tolerance, are also defined.

A plurality of vectors are defined in the time series of N data points, each vector comprising m consecutive points and also serving as a template vector for comparison with all other vectors including itself. This process is referred to as self-matching, in the time series, and leads to the determination of a conditional probability (condition that the distance between the template vector and the conditioning vectors are within the tolerance 'r' associated with this vector).

In what follows Approximate Entropy is noted ApEn.

Step 1. Form N−m+1 vectors X(1), . . . , X(N−m+1) defined by: $X(i)=[x(i), x(i+1), \ldots, x(i+m-1)]$ and i=1, . . . , N−m+1. Fix m, an integer, and r, a positive real number. The value of m represents the window length of compared run of data, and r specifies a filtering level.

Step 2. Define the distance d[X(i),X(j)] between X(i) and X(j), as the maximum norm: $d[X(i),X(j)]=\max_{k=1, 2, \ldots, m}|X(i+k-1)-X(j+k-1)|$. The variable d represents the distance between the vectors x(i) and x(j), given by the maximum difference in their respective scalar components.

Step 3. For a given X(i), count the number so that $d[X(i),X(j)] \leq r$, denoted as $N^m(i)$. Then, for i=1 . . . N−m+1, is $$C_r^m(i) = \frac{N^m(i)}{(N-m+1)}$$

$C_r^m(i)$ measures, within a tolerance r, the frequency of patterns similar to a given window of length m.

Step 4. Compute the natural logarithm of each $C_r^m(i)$ and average it over i, $$\phi^m(r) = \frac{1}{N-m+1} \sum_{i=1}^{N-m+1} \ln C_r^m(i)$$

where, $C_r^m(i)$ is the probability of vector $X_j^m$ to lie within a distance r of the vector $X_i^m$ Step 5. We define the entropy vector as the vector of entropy value by the window of length m and it is assigned to the vector in time (t+m/2)

$$VecEn\left(t+\frac{m}{2}\right) = \phi^m(r)$$

Step 6. Increase the dimension to m+1. Repeat steps (1) to (4) and find $C_r^{m+1}(i)$ and $\phi^{m+1}(r)$.

Step 7. ApEn is defined by:
$$ApEn(m,r,N)=\phi^m(r)-\phi^{m+1}(r)$$

Although the selection of m and r are critical in computing ApEn, there are no proper guidelines to optimize these values. For smaller r values, poor conditional probability estimates are achieved whereas for larger r values, detailed system information is lost. To avoid a significant contribution of noise in ApEn computation, value of r should be chosen such that it is larger than most of the noise present in the signal. It was suggested to estimate ApEn with parameter values m=2 and r=0.2*SD where SD represents the standard deviation of the original data sequence {x(n)}.

Back to FIGS. 3a and 3b, the last graph of each figure represents the value of approximate entropy computed over the signal r(t) of the previous graph, with a window length of 300 ms for example. The value of approximate entropy computed over all the signal on FIG. 3a is 9.97 whereas the value of entropy computed over all the signal on FIG. 3b is 16.63. The second driver, which data regarding visual exploration strategy are displayed in FIG. 3b, therefore exhibits a poorer efficiency of visual exploration strategy than the first driver, which data are displayed in FIG. 3a.

Values of entropy with time may also be computed in order to assess the evolution of entropy with time. This computation is performed according to the following steps:

For a given time series data of length N, form N–m vectors of length m each:

$$X(1) = \{x(1), x(2), \ldots, x(m)\}$$
$$X(2) = \{x(2), x(3), \ldots, x(m+1)\}$$
$$\ldots$$
$$X(N-m+1) = \{x(N-m+1), x(N-m+2), \ldots, x(N)\}$$

Each of the vectors X is composed of m consecutive and discrete data points of the time series of length N, and embedding dimension bin number M.

Take each vector X and divide it into M numbers of equally spaced bins and the corresponding histogram is obtained.

Now, at each bin i of the histogram, its probability is estimated, $$p_i = \frac{\text{count in bin } i}{\text{total number of elements in matrix}}; \ 1 \leq i \leq M$$

By the definition of Shannon Entropy, the entropy of a given time series is defined by the expression $S(X) = \Sigma_{i=1}^{m} p_i \log p_i$, where $p_i$ is the probability of each bin in the histogram.

this entropy value is assigned to the vector VecEn $VecEn(t) = S(X_t^m))$ where $1 \leq t \leq N-m$ and $X_i^m$: $1 \leq i \leq (N-m)$.

In some embodiments, in addition to the approximate entropy of the gaze direction of observed spot, the approximate entropy of the eyes motion and the approximate entropy of the head motion may be computed.

The relative values of the approximate entropy of the eyes and motion may be compared to identify which of the motion of the eyes and of the motion of the head has poorer efficiency, which has an impact on the visual exploration strategy and the ophthalmic device that will be most comfortable for the wearer.

Figure 4:
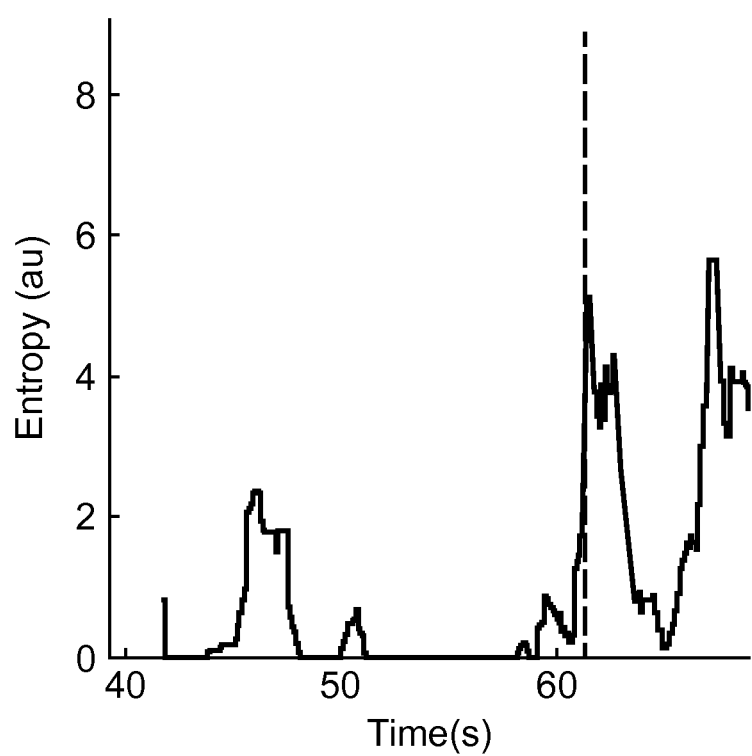
FIG. 4 represents an example of entropy evolution in time of a visual exploration strategy involved during a test situation.

With reference to FIG. 4, another indicator of an efficiency of the visual exploration strategy is the evolution with time of entropy. An increase with type of the entropy of the visual exploration strategy (for instance the entropy of the gaze direction) tends to show that the visual exploration strategy is not robust with time and that it is going to make the wearer more tired or uncomfortable. The evolution of entropy can also reveal the fragility of a visual exploration strategy when the task becomes too complex or uncertain.

According to another embodiment, the criterion for evaluating the efficiency of the visual exploration strategy could also be the measure of Lempel-Ziv complexity, introduced in the article "On the complexity of finite sequences" IEEE Transactions on Information Theory 22(1) (1976) 75-81.

So, an indicator of an efficiency of the visual exploration strategy can be determined from the spectral decomposition analysis of a signal representative of the visual exploration, such as the recorded gaze direction or the recording of the eyes motion, or the computed Approximate Entropy of such signal. For instance, a criterion assessing the efficiency of the visual exploration strategy can be, as explained below, a power index computed from the power spectrum of the considered signal, or a number of frequencies involved in the considered signal.

Below is an exemplary spectral analysis of a signal representative of the visual exploration. In this example the signal is a gaze direction signal, however the same processing can be performed on the other signals recited above.

A sinusoidal signal, $s(t) = \alpha \cos(\omega t + \phi)$ can be rewritten as a linear combination of two complex-valued sinusoidal signals, $s(t) = \alpha_1 e^{i(\omega t + \phi_1)} + \alpha_2 e^{i(\omega t + \phi_2)}$, whose parameters are constrained as follows:

$$\alpha_1 = \alpha_2 = \frac{\alpha}{2} \quad (1.11)$$
$$\phi_1 = \phi_2 = \phi$$
$$\omega_1 = -\omega_2 = \omega$$
$$i = \sqrt{-1}$$

The fact that we need to consider two constrained complex sine waves to treat the case of one unconstrained real sine wave shows that the real-valued case of sinusoidal signals can actually be considered to be more complicated than the complex-valued case.

If we consider discrete signals (gaze signal detected). Such signals are most commonly obtained by the temporal or spatial sampling of a continuous (in time or space) signal.

$$\tilde{g}(\rho, t) = \Sigma_{t=1,2,3}{}^N \rho_t \quad (1.12)$$

$\tilde{g}(\rho, t)$ denotes a deterministic discrete-time gaze data sequence.

Assume that $\tilde{g}(\rho, t)$ has finite energy, which means that $$\Sigma_{t=-\infty}{}^{+\infty} |\tilde{g}(\rho, t)|^2 < \infty \quad (1.13)$$

Then, under some additional regularity conditions, In general the sequences {g(t)} possesses a Discrete-Time Fourier Transform (DTFT) defined as:

$$G(w) = \Sigma_{t=-\infty}{}^{+\infty} g(t) e^{-i\omega t} \quad (1.14)$$

And the corresponding inverse DTFT is then $$g(t) = \frac{1}{2\pi} \int_{-\pi}^{\pi} G(w) e^{iwt} dw \quad (1.15)$$

The angular frequency w is measured in radians per sampling interval. The conversion from w to the physical frequency variable $\bar{w} = w/T_s$ (rad/sec). The corresponding Energy Spectral Density is then:

$$S(w) = |Y(w)|^2 \quad (1.16)$$

This equation can be restated as:

$$\sum_{t=-\infty}^{+\infty} |g(t)|^2 = \frac{1}{2\pi} \int_{-\pi}^{\pi} S(w) dw \quad (1.17)$$

This equality is called Parseval's theorem. It shows that S(w) represents the distribution of sequence energy as a function of frequency. For this reason, S(w) is called the energy spectral density.

The discrete time signal g(t); t=0, ±1, ±2, . . . , ±N is assumed to be a sequence of random variables with zero mean and the auto covariance sequence (ACS) or covariance function of g(t) is defined as $$r(k)=E\{g(t)g^*(t-k)\} \quad (1.20)$$

Where E{.} denotes the expectation operator, and it is assumed to depend only on the lag between the two samples averaged (Priestley, 1989).

Now, the power spectral density (PSD) is defined as the DTFTF of the covariance sequence:

$$\phi(w)=\Sigma_{t=-\infty}^{+\infty} r(k)e^{-iwk} \quad (1.21)$$

The inverse transform, which recovers {r(k)} from given ϕ(w), is $$r(k) = \frac{1}{2\pi} \int_{-\pi}^{\pi} \phi(w) e^{iwk} dw \quad (1.22)$$

From (1.22) we can obtain r(0)=E|g(t)|² if k=0:

$$r(0) = \frac{1}{2\pi} \int_{-\pi}^{\pi} \phi(w) dw \quad (1.23)$$

measures the (average) power of {g(t)}, the (1.23) shows that ϕ(w) can indeed be named PSD, as it represents the distribution of the (average) signal power over frequencies.

Put another way, it follows from (1.23) that ϕ(w)dω/2π is the infinitesimal power in the band (ω−dω/2, ω+dω/2), and the total power in the signal is obtained by integrating these infinitesimal contributions. The thus-obtained total power of the signal is the power index cited above that is computed out of the power spectrum of the signal and is indicative of the efficiency of visual exploration strategy. In embodiments, the power index can be normalized to exhibit a value ranging between 0 and 1 in order to make its comparison easier and more accurate.

Figure 8A:
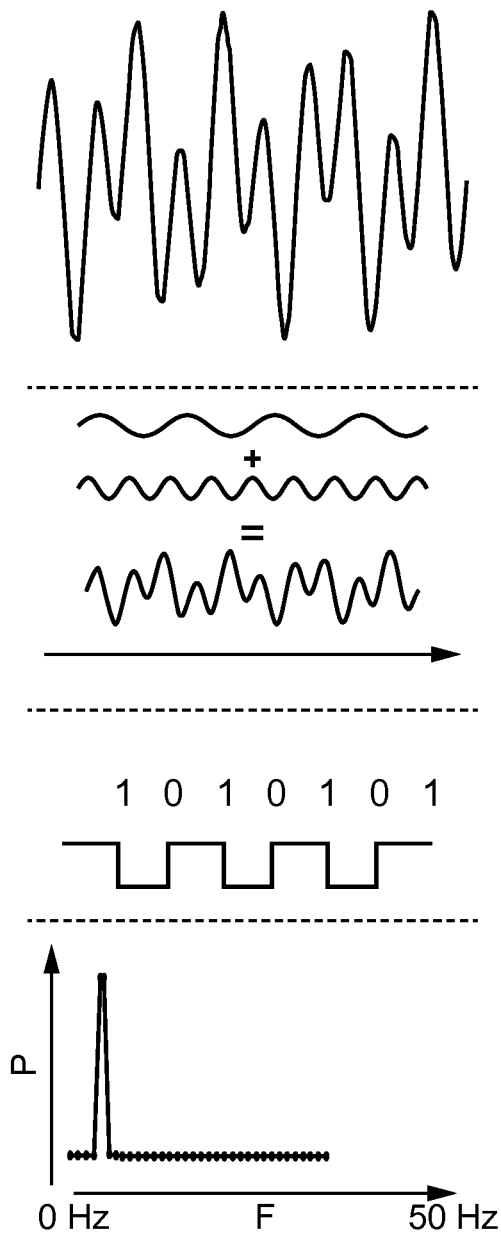
FIGS. 8a and 8b show the processing of two theoretical signals to obtain the power index of approximate entropy of each signal.
Figure 8B:
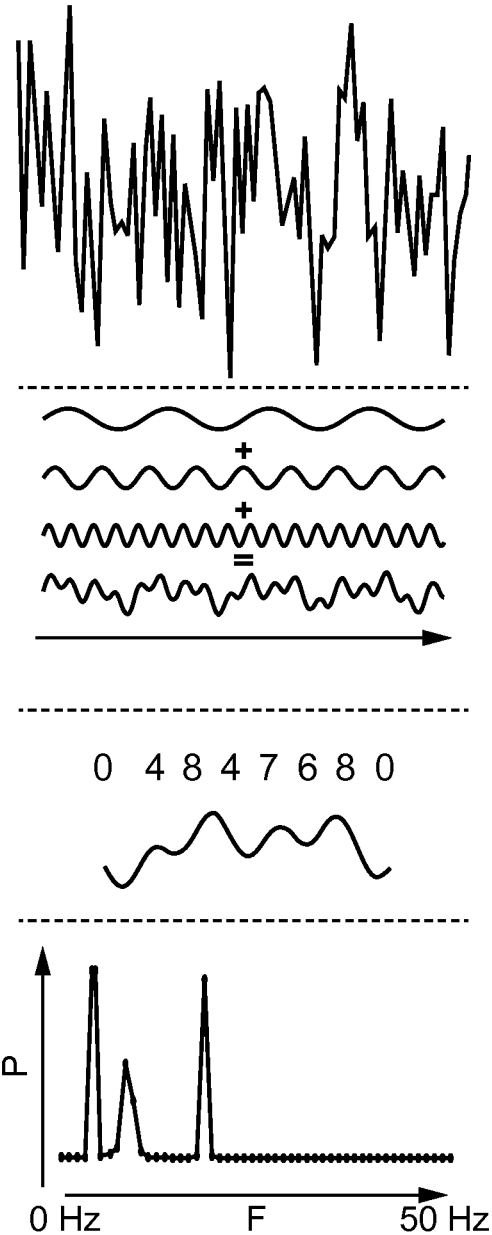

With reference to FIGS. 8a and 8b, is shown a theoretical example of the spectral decomposition and power index computation of two Approximate entropies computed respectively from two signals. The base signal of FIG. 8a comprises fewer frequencies than the signal of FIG. 8b. In both figure, the first line corresponds to the recorded signal, such as, in the case of the invention, a gaze direction signal. The second line represents a decomposition of the signal in sinusoids. The third line represents an Approximate entropy of the signal, and the last line represents the power of the approximate entropy against frequency. The power index is the integral of this plot and corresponds to the area under the curve, which can be normalized. As can be readily understood from this theoretical example, the power index will be higher for a signal recorded from a poorly efficient visual exploration strategy, because it comprises more frequencies, than for a signal recorded from a highly efficient visual exploration strategy.

The power spectral density of the signal can also be used to build a so-called phasor plot of the signal, defined below.

Since (1.21) {ϕ(w)} is a power density, it should be real-valued and nonnegative. That this is indeed the case is readily seen from definition of ϕ(w). Hence, $$\phi(w) \geq 0 \text{ for all } w \quad (1.24)$$

Using (1.21), we obtain:

$$\phi(w)=r(0)+2\Sigma_{k=-\infty}^{+\infty} Re\{r(k)e^{-iwk}\} \quad (1.25)$$

where Re{.} denotes the real part of the bracketed quantity. If g(t), and hence r(k), is real valued then it follows that:

$$\phi(w)=r(0)+2\Sigma_{k=-\infty}^{+\infty} r(k)\cos(wk) \quad (1.26)$$

which shows that ϕ(w) is an even function in such a case. In the case of complex-valued signals, however, ϕ(w) is not necessarily symmetric about the w=0 axis.

For real valued signal: ϕ(w)=ϕ(−w), w∈[−π,π]

For complex-valued signals: ϕ(w)≠ϕ(−w), w∈[−π,π]

On the other hand, our motivation for considering spectral analysis is to characterize the average power at frequency ω in the signal. The above definitions can be extended quite directly to the case of random signals such as a gaze direction.

A phasor is a complex number representing a sinusoidal function whose amplitude (A), angular frequency (w) and initial phase θ are time-invariant. It is related to a more general concept called analytic representation. Euler's formula indicates that sinusoids signals can be represented mathematically as the sum of two complex-valued functions:

$$A\cos(wt + \theta) = A\frac{e^{i(wt+\theta)} + e^{-i(wt+\theta)}}{2} \quad (1.27)$$

Or as the real part of one of the function:

$$A\cos(wt+\theta)=Re\{Ae^{i(wt+\theta)}\}=Re\{Ae^{i\theta} \cdot e^{iwt}\} \quad (1.28)$$

The function $Ae^{i(wt+\theta)}$ is called the analytic representation of Acos(wt+θ). It is sometimes convenient to refer to the entire function as a phasor (see also Singh, Ravish R, "Section 4.5: Phasor Representation of Alternating Quantities", Electrical Networks, Mcgraw Hill Higher Eduction, 2009, p. 4.13., ISBN 0070260966).

During the data capture, the eye tracker captures the noisy n(x,y) gaze coordinates on a plane (monitor) reported by the eye tracker and can be represented as $$g=[(x_1,y_1),(x_2,y_2), \ldots ,(x_n,y_n)] \quad (1.29)$$

Figure 5A:
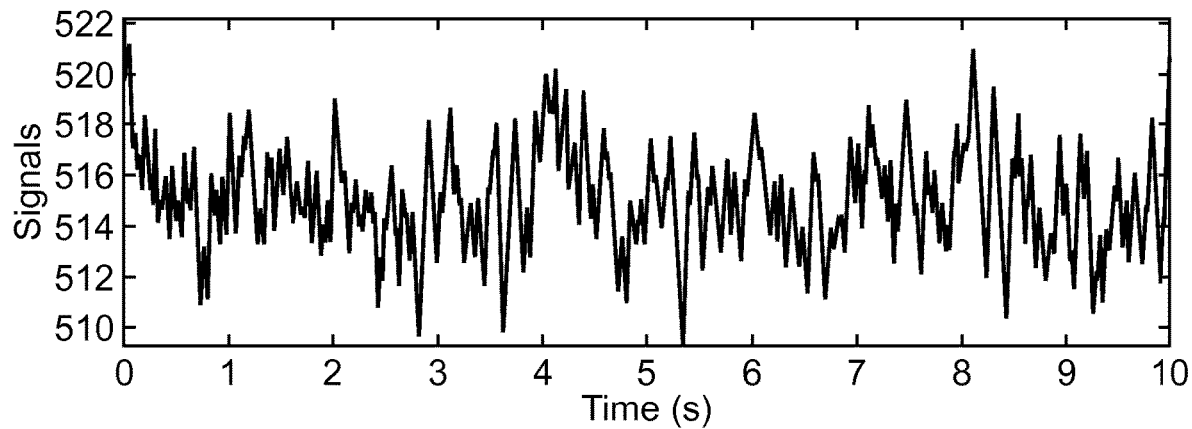
FIG. 5a represents an exemplary signal of gaze direction with time.
Figure 5B:
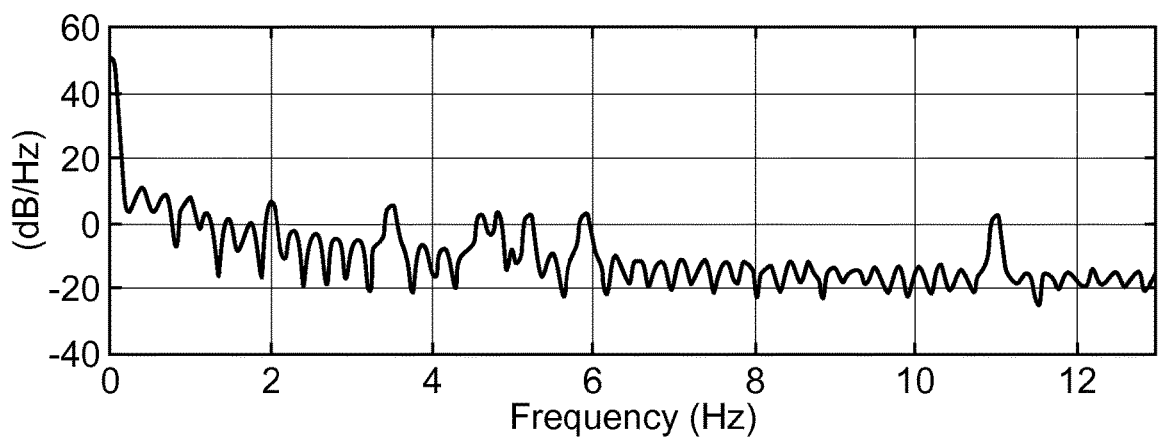

In view of the above, the following steps may be performed in order to perform spectral analysis of the recording of the gaze direction of the wearer, an example of which is shown in FIG. 5a:

Calculating the power spectral density PSD (with the method described above or any other method that calculates PSD)—FIG. 5b Once the PSD is calculated, choosing the frequency bands in which the signal will be decomposed, and applying Band Pass Filters or algorithms such as wavelet transform to get exactly the desired frequency ranges.

Figure 5C:
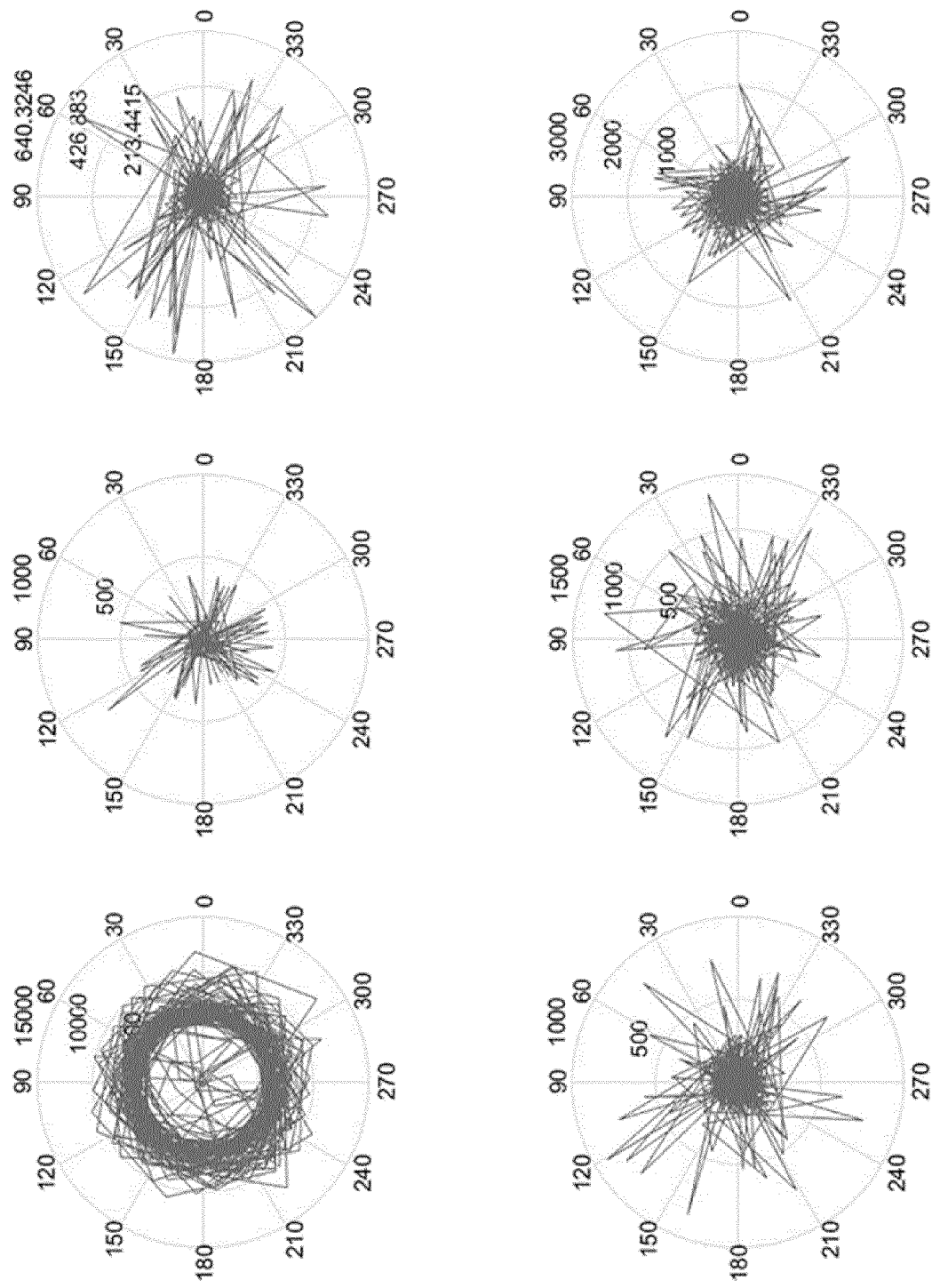
FIGS. 5c and 5d represent phasors of visual exploration acquired for two distinct lens designs, FIGS. 6a schematically represents an example of simulation of a test situation using a virtual reality device.
Figure 5D:
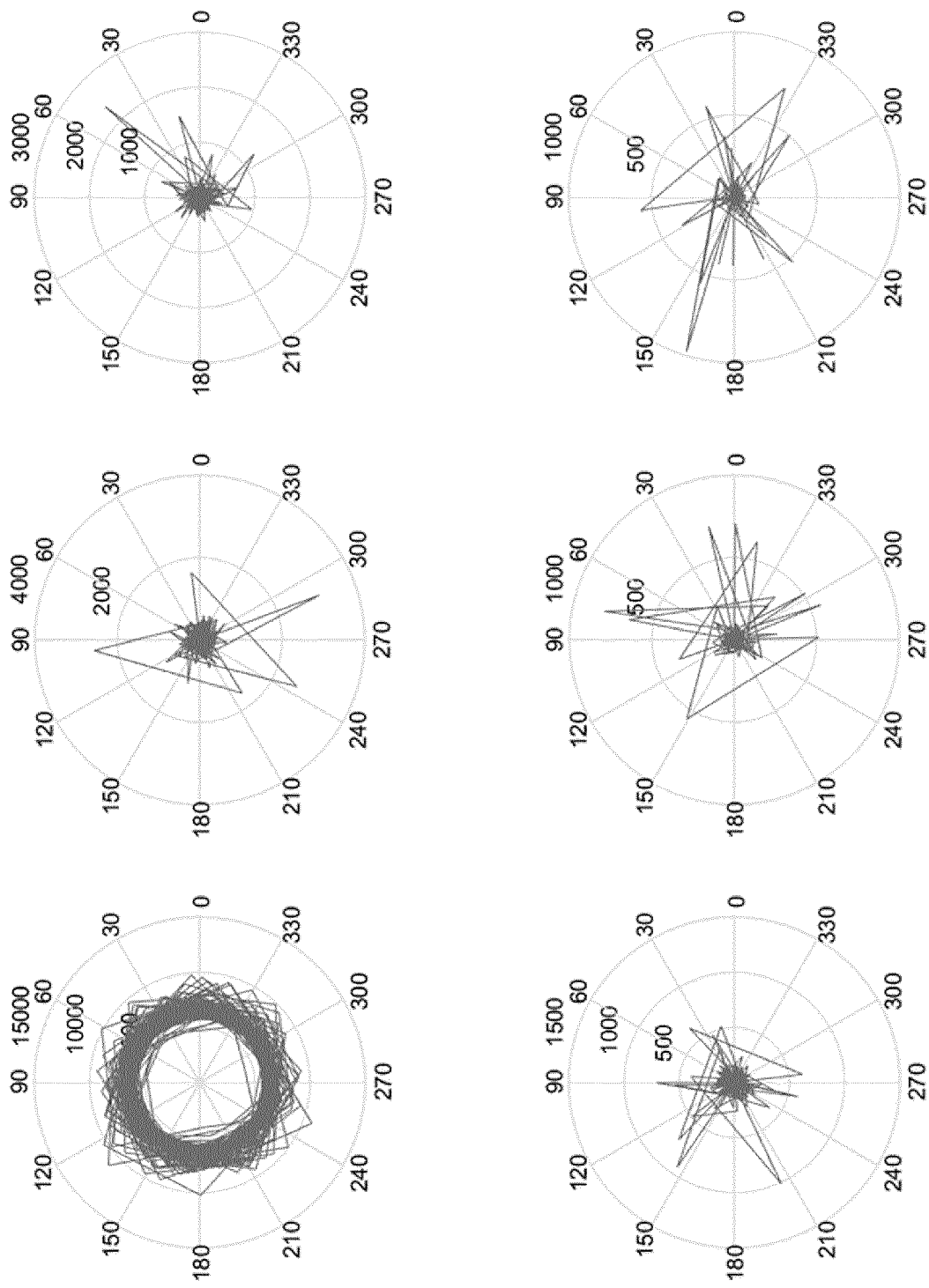

Selecting the frequencies of greater spectral power,

Once the signals for each frequency band are obtained, it is possible to plot the signals in phasor form as shown in FIGS. 5c and 5d.

As an illustrative example but not limitative, we compare lens designs having a short (Lens A) vs. a long progressive corridor (Lens B). Phasor plots are represented for the six main frequencies of each signal acquired for lens A and lens B, respectively in FIGS. 5c and 5d. The selection of the most adapted lens for the wearer may be based on the breakdown number appearing in the main frequency of the visual exploration. As illustrated in FIG. 5d in the left top phasor plot, lens B is more appropriate.

According to still another embodiment, an indicator of an efficiency of the visual exploration strategy can be efficiency in transiting from one observed area of interest to another.

To evaluate this indicator, a number N of areas of interest ("AOI") of the wearer's field of view are identified, which are the zones more frequently observed by the wearer.

Figure 6B:
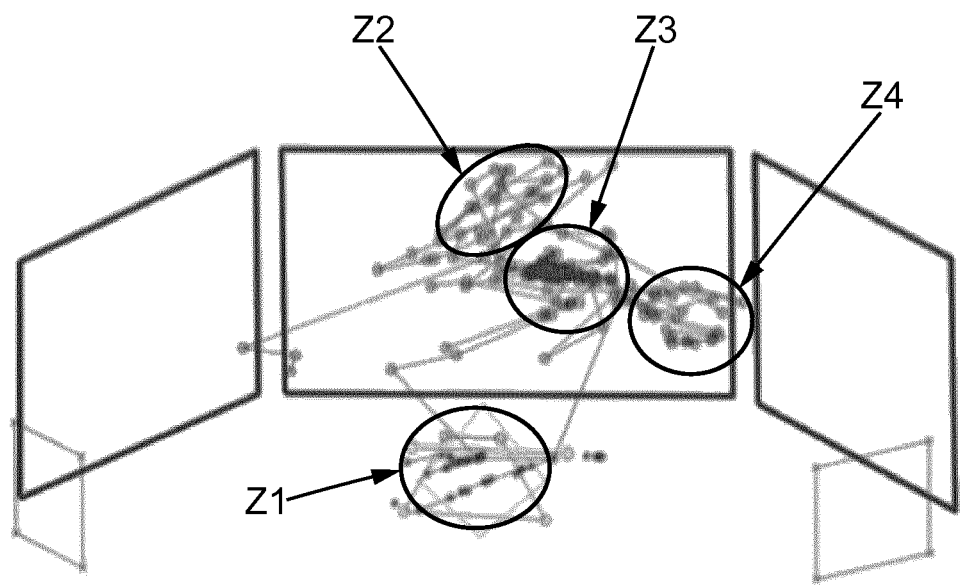

With reference to FIG. 6b, an example of recording of a visual exploration strategy of a wearer during a test scenario simulated using a virtual reality equipment 4 is shown. From the spots which are the most frequently observed by the wearer it is possible to identify zones of interest such as the zones Z1, Z2, Z3 and Z4 identified on the figure.

A Markov Chain of the zones is then formed, where each zone is associated to a set of probabilities to transit to other zones at a next time. The Markov Chain satisfies the following equation, where $X_n$ denotes the zone of interest observed by the wearer at time n:

$$P(X_{n+1}=x_{n+1}|X_n=x_n, \ldots, X_0=x_0)$$

The efficiency in transiting from one zone of interest to another can then be evaluated from the zones contained in a visual exploration path followed by the wearer from the zone to the other, their associated probabilities and their locations relative to the considered zones of interest.

In an embodiment, a stationary entropy given by Krejtz et al in "Entropy-based statistical analysis of eye in movement transitions", in Proceedings of the Symposium on Eye Tracking Research and applications (ETRA'14), 2014, may be computed. The stationary distribution is the vector means probabilities that the gaze converges on each AOI when the user's gaze transition diverges to infinity. This value can be calculated from the transition matrix, and it means what zones of interest attract a user's gaze. Suppose transition matrix P, the stationary distribution $\pi$ derived from P, and the state space $\varphi$ (zones of interests), where $i \in \varphi$. We can get the entropy of the stationary distribution as follows:

$$H_s = \Sigma_{i \in \varphi} \pi_i \log \pi_i$$

If the value of $H_s$ is high, it means that transitions occur between different (or even all) AOIs. If the value is low, fixations tend to be kept on certain AOIs, and transitions only happen between a few AOIs, so the efficiency of the visual exploration strategy is greater (see also article by Gilland J, "Driving, Eye Tracking and Visual Entropy: Exploration or Age and tasks effects", University of South Dakota, 2008).

Preferably, in order to compare the entropy value of different systems, it is necessary to establish a common metric for all. It can be performed through a simple normalization, i.e. by dividing the empirical entropy $H_{Obs}$ by the theoretical maximum value of entropy $H_{max}$ for the estimate or the modeled state space:

$$H_r = \frac{H_{obs}}{H_{max}}$$

This relative value of entropy Hr allows comparing results between different groups and different situations. High entropy will mean all combinations are close to equiprobable. Low entropy will mean redundancy and high probabilities of only a few combinations.

Additionally, the total fixation time for each AOI may also be computed in order to complete the analysis of the visual exploration strategy.

It results from the above that quite a number of different criteria can be evaluated by processing a recording of a visual exploration strategy, in order to assess the efficiency of the visual exploration strategy.

As a summary, the different criteria detailed above as well as their specificities are listed below.

value of Approximate Entropy computed on a recording of gaze direction, eye motion, or heat motion; this criterion allows global assessment of the visual exploration and is sensitive to visuo-cognitive skills, blur and reduced visual acuity.

changes or evolution of Approximate Entropy computed on a recording of gaze direction, eye motion, or head motion; this criterion allows an assessment over a time windows enabling to assess changes in efficiency. It is hence sensitive to chances such as visual fatigue, changes in visual and/or cognitive, motor skills and performances, to exogenous cues such as danger.

PSD or phasor plot obtained from the same, which can be computed on a recording of gaze direction, eye motion or head motion or on an Approximate Entropy computed therefrom. This criterion allows assessing the weight and redundancy of each frequency comprised on the examined vector. It can further help assessing sub visual exploration components such as particular frequencies revealing specific eye movement patterns or head motion control.

Power-based index computed on a recording of gaze direction, eye motion or head motion or on an Approximate Entropy computed therefrom; this criterion allows global assessment of the visual exploration. When computed based on approximate entropy, it is sensitive to visuo-cognitive skills that reflect the frequencies' weights included in the entropy vector and the energy expenditure across the signal Efficiency in transiting from one observed area to another, evaluated from a Markov Chain of the areas of interest that were explored during visual exploration, this criterion enables assessing a visual exploration randomness and a redundancy inside specific spatial areas of interest.

Entropy of the distribution of the Markov Chain describes the randomness or efficiency of the visual exploration across all areas of interests.

Thus depending on the needs, it may be advantageous to combine different criteria in order to assess different aspects of the efficiency of the evaluation strategy.

Figure 2:
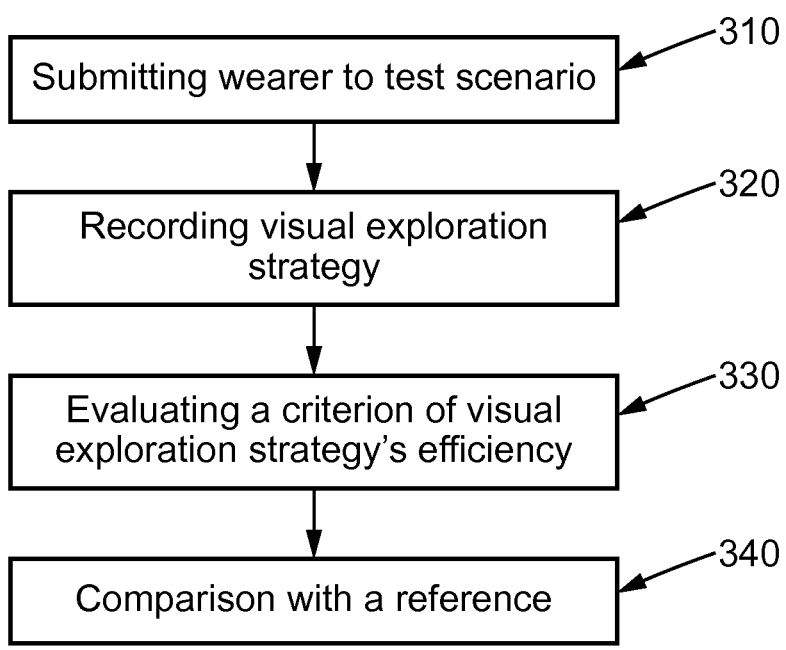

Back to FIG. 2, in an embodiment, when the criterion assessing visual exploration strategy has been evaluated, the value of the criterion may be compared during a step 340 with a reference value.

For instance, the value may be compared with a reference value previously determined on the same wearer, with the same test scenario, or at least a scenario having the same task, same environment and generally the same mental load or the same type of additional tasks. The test scenarios are indeed randomized in order to keep a surprise effect when needed and to prevent the wearer from adapting its visual exploration strategy to a scenario he already knows.

According to an example, the reference value may have been acquired with the wearer wearing no ophthalmic device or wearing a previous ophthalmic device, and the value determined at step 330 may be acquired with the wearer testing a new ophthalmic device.

The reference value may also be a value computed over a population having parameters values similar to those of the wearer. In this case, reference values for a plurality of populations are stored in a database 2 and the reference value which is the most relevant to the wearer is retrieved by interrogating the database 2 using at least some of the parameter values relating to the wearer.

In this case the value of the visual exploration strategy efficiency of the wearer may have been determined with the wearer wearing a current ophthalmic device or testing a new ophthalmic device.

As explained in more details below, the outcome of the comparison, if any, is taken into account for personalizing an ophthalmic device of the wearer.

According to another embodiment of step 300, the determination of a value of a criterion assessing the visual exploration strategy efficiency of a wearer may be performed by interrogating a database in which reference values, such as for instance average values of the criterion are stored for a plurality of populations. The interrogation of the database can be performed using the set of parameters values relating to the wearer in order to retrieve a reference value computed for a population which is the most relevant to the wearer.

In this case, the value determined for the wearer corresponds to the reference value stored in the database for the population having parameters values closest to those of the wearer.

Back to FIG. 1, the method then comprises a step determining an optical design of an ophthalmic device to be worn by the wearer according to the evaluated criterion assessing the efficiency of its visual exploration strategy.

This method may also be performed in a number of different ways according to the preceding steps of the method.

According to an embodiment, the selection or the personalization of the design of the ophthalmic device may be performed in order to increase the efficiency of the visual exploration strategy. To do this, a number of devices may be tested on the wearer, and the efficiency of the visual exploration strategy may be evaluated to select the device allowing the best efficiency.

If step 300 comprised a comparison of the efficiency of the visual exploration strategy of the wearer with a reference corresponding to a population having characteristics similar to the wearer, the selection or personalization of the design may also be performed in order to bring the efficiency of the wearer's visual exploration strategy as close as possible to the reference value, if said efficiency initially is lower than the reference value.

According to another example, if a comparison was performed between the efficiency of the visual exploration strategy of the wearer with a previous ophthalmic device and with a test device, the selection may be performed to increase the efficiency obtained with the test device as compared to the previous one.

According to an embodiment, the selection or personalization of the design of the ophthalmic device may also be performed by adjusting a particular design parameter of the ophthalmic device according to the efficiency of the visual exploration strategy that has been measured.

For instance, if it has been evaluated that the wearer has poor efficiency in transiting from one visual zone to another (such as for instance a near vision zone and a far vision zone), the personalization of the design may comprise the adjustment of the geometry of each zone and reducing the aberrations between the zones to improve the efficiency in transiting between the two zones, in order to reduce the astigmatism along the progression corridor.

According to another example, if a value of entropy has been measured for the head and the eyes motions, and if it is noticed that one system presents a poorer efficiency compared to the other, this can be taken into account for the design of the ophthalmic device. If the head motion decreases the efficiency of the visual exploration then a progressive addition lenses with a smoother aberration repartition will be proposed, whereas if the eyes motions decreases the efficiency of the visual exploration design with larger visual field will be proposed.

The efficiency of the visual exploration strategy for a given wearer can depend upon the wearer's capacity to adapt, hence an adaptation phase can also be implemented, once an ophthalmic device has been chosen, to regularly check the evolution of the efficiency of the visual exploration strategy of the wearer equipped with this design.

What is claimed is:

1. A method for determining an adapted ophthalmic device for a wearer, the method comprising:
   acquiring a set of parameters values relating to the wearer;
   determining at least a task to be performed by the wearer involving visual exploration;
   using a computing system, determining a value of a criterion assessing an efficiency of the wearer's visual exploration strategy for said task; and
   determining an optical design of an ophthalmic device to be worn by the wearer according to the determined value of the criterion, wherein
   the criterion assessing the efficiency of the wearer's visual exploration strategy is chosen among a group consisting in:
   an approximate entropy of the visual exploration,
   power based index of the visual exploration or of the approximate entropy of the visual exploration, determined from energy expenditure in a signal,
   a number, weight and redundancy of frequencies involved in a visual exploration pattern, determined from a spectral analysis of recorded visual exploration or on the approximate entropy of the visual exploration,
   an evolution on time of the approximate entropy of the visual exploration, or
   an efficiency in transiting from one observed zone of interest to another.

2. The method according to claim 1, wherein the determining the value of the criterion assessing the efficiency of the wearer's visual exploration strategy for said task comprises:
   submitting the wearer to a test scenario involving performance of said task in a determined environment,
   recording, with at least one sensor, the wearer's visual exploration strategy during the test scenario, and evaluating the criterion assessing the efficiency of the wearer's visual exploration strategy from the recorded visual exploration strategy.

3. The method according to claim 2, wherein
the determining the value of the criterion assessing an efficiency of the wearer's visual exploration strategy further comprises comparing the evaluated criterion to a reference value, and
the determining the optical design is performed according to an outcome of the comparison of the evaluated criterion and the reference value.

4. The method according to claim 3, wherein the reference value is calculated over a reference population, or is a reference value for the wearer.

5. The method according to claim 4, wherein the reference value is assessed from the wearer's visual exploration strategy during a previous submission of the wearer to a test scenario involving the performance of a same task in a same determined environment, the wearer being equipped with a previous ophthalmic device or being devoid of any ophthalmic device.

6. The method according to claim 2, wherein the recording the wearer's visual exploration strategy comprises recording, at a determined frequency, a gaze direction or spot observed by the wearer.

7. The method according to claim 6, wherein the recording the wearer's visual exploration strategy further comprises recording, at a determined frequency, a motion of eyes and of a head of the wearer.

8. The method according to claim 2, wherein the submitting the wearer to a test scenario involving the performance of said task in the determined environment is performed by submitting the wearer to a virtual situation simulated using a virtual reality equipment.

9. The method according to claim 2, wherein the test scenario is configured based on:
a selection of the task to be performed while the visual exploration strategy is recorded,
a selection of the environment, in which the task is performed, and
a selection of at least one additional parameter affecting the visual exploration involved during the test situation, among a group of parameters comprising:
duration of the test scenario,
visual scene complexity of the test scenario,
number and disposition of zones of interest to be explored in the environment while performing the selected task,
mental work load, or
type and number of decisions to be performed by the wearer during the test scenario.

10. The method according to claim 1, wherein
the determining the value of the criterion assessing the efficiency of the wearer's visual exploration strategy for said task, is performed using a system comprising a computer and a database storing reference values of the criterion assessing the visual exploration strategy efficiency for each of a plurality of populations of wearers and each of a plurality of tasks, and
the determining the value of the criterion assessing the efficiency of the visual exploration strategy of the wearer comprises interrogating, with the computer, the database with input data comprising the set of parameter values relating to the wearer and the task, to retrieve a reference value of the criterion for a population corresponding to the wearer.

11. The method according to claim 1, wherein the determining the optical design comprises choosing, among a plurality of designs of the ophthalmic device, a design maximizing the efficiency of the wearer's visual exploration strategy for the task.

12. The method according to claim 1, further comprising determining a value of at least two different criteria assessing an efficiency of the wearer's visual exploration strategy for said task, and determining the optical design of the ophthalmic device to be worn by the wearer according to the determined values of the criteria.

13. The method according to claim 1, wherein the criterion assessing the efficiency of the wearer's visual exploration strategy is the efficiency in transiting from one observed zone of interest to another, and the evaluation of the criterion comprises:
determining a plurality of areas of interest of the wearer's field of view,
recording, with at least one sensor, the wearer's visual exploration strategy during the test, and computing a proportion of occurrences within the areas of interest,
forming a Markov Chain of the areas of interest, wherein each area of interest is associated to a set probabilities to transit to other zones at a next time, and
evaluating the efficiency in transiting from one area of interest to another from a processing of the Markov Chain of the areas of interest.

14. The method according to claim 13, wherein the processing of the Markov Chain comprises computing an entropy of a stationary distribution of the areas of interest.

15. The method according to claim 1, further comprising:
evaluating approximate entropy of gaze direction or spot observed by the wearer;
evaluating approximate entropy of a motion of eyes of the wearer; and
evaluating approximate entropy of a motion of a head of the wearer,
wherein the determining the optical design of the ophthalmic device to be worn by the wearer is performed based on the approximate entropy of gaze direction or spot observed by the wearer, and based on relative values of the approximate entropy of a motion of eyes and the approximate entropy of motion of the head.

16. A system for determining an adapted ophthalmic device for a wearer, the system comprising:
a computing device configured to:
receive a set of parameter values relating to the wearer,
receive additional input data comprising at least identification of a task to be performed by the wearer and involving visual exploration, and
determine a value of a criterion assessing an efficiency of the wearer's visual exploration strategy for said task from the set of parameter values and the additional input data,
wherein
the criterion assessing the efficiency of the wearer's visual exploration strategy is chosen among a group consisting in:
an approximate entropy of the visual exploration,
power based index of the visual exploration or of the approximate entropy of the visual exploration, determined from energy expenditure in signal,
a number, weight and redundancy of frequencies involved in a visual exploration pattern, determined from a spectral analysis of recorded visual exploration or on the approximate entropy of the visual exploration, an evolution on time of the approximate entropy of the visual exploration, or an efficiency in transiting from one observed zone of interest to another.

17. A method for determining an adapted ophthalmic device for a wearer, the method comprising:
acquiring a set of parameters values relating to the wearer;
determining at least a task to be performed by the wearer involving visual exploration;
using a computing system, determining a value of a criterion assessing an efficiency of the wearer's visual exploration strategy for said task; and
determining an optical design of an ophthalmic device to be worn by the wearer according to the determined value of the criterion, wherein
the determining the optical design comprises choosing, among a plurality of designs of the ophthalmic device, a design maximizing the efficiency of the wearer's visual exploration strategy for the task.

18. A method for determining an adapted ophthalmic device for a wearer, the method comprising:
acquiring a set of parameters values relating to the wearer;
determining at least a task to be performed by the wearer involving visual exploration;
using a computing system, determining a value of a criterion assessing an efficiency of the wearer's visual exploration strategy for said task; and
determining an optical design of an ophthalmic device to be worn by the wearer according to the determined value of the criterion, wherein
the method further comprises:
evaluating approximate entropy of gaze direction or spot observed by the wearer;
evaluating approximate entropy of a motion of eyes of the wearer; and
evaluating approximate entropy of a motion of a head of the wearer, and
the determining the optical design of the ophthalmic device to be worn by the wearer is performed based on the approximate entropy of gaze direction or spot observed by the wearer, and based on relative values of the approximate entropy of a motion of eyes and the approximate entropy of motion of the head.

19. A system for determining an adapted ophthalmic device for a wearer, the system comprising:
a computing device configured to:
receive a set of parameter values relating to the wearer,
receive additional input data comprising at least identification of a task to be performed by the wearer and involving visual exploration, and
determine a value of a criterion assessing an efficiency of the wearer's visual exploration strategy for said task from the set of parameter values and the additional input data, wherein an optical design is determined by choosing, among a plurality of designs of the ophthalmic device, a design maximizing the efficiency of the wearer's visual exploration strategy for the task.

20. A system for determining an adapted ophthalmic device for a wearer, the system comprising:
a computing device configured to:
receive a set of parameter values relating to the wearer,
receive additional input data comprising at least identification of a task to be performed by the wearer and involving visual exploration, and
determine a value of a criterion assessing an efficiency of the wearer's visual exploration strategy for said task from the set of parameter values and the additional input data,
wherein
the computing device is further configured to
evaluate approximate entropy of gaze direction or spot observed by the wearer,
evaluate approximate entropy of a motion of eyes of the wearer, and
evaluate approximate entropy of a motion of a head of the wearer, and
an optical design of the ophthalmic device to be worn by the wearer is determined based on the approximate entropy of gaze direction or spot observed by the wearer, and based on relative values of the approximate entropy of a motion of eyes and the approximate entropy of motion of the head.

* * * * *